(12) United States Patent
Leventhal et al.

(10) Patent No.: US 8,216,291 B1
(45) Date of Patent: Jul. 10, 2012

(54) APPARATUS AND METHOD OF PROVIDING THERAPEUTIC IMMERSIVE, VIBRATORY AND HEAT TREATMENT TO A BODY PART

(76) Inventors: Robert D. Leventhal, Los Angeles, CA (US); Paul B. Thomas, San Pedro, CA (US)

( * ) Notice: Subject to any disclaimer, the term of this patent is extended or adjusted under 35 U.S.C. 154(b) by 1539 days.

(21) Appl. No.: 11/710,031

(22) Filed: Feb. 23, 2007

Related U.S. Application Data

(63) Continuation-in-part of application No. 09/962,464, filed on Sep. 25, 2001.

(51) Int. Cl.
*A61F 7/00* (2006.01)
(52) U.S. Cl. ........ 607/111; 607/104; 607/110; 607/112; 607/114
(58) Field of Classification Search .................... 607/81, 607/84–86
See application file for complete search history.

(56) References Cited

U.S. PATENT DOCUMENTS

| | | | |
|---|---|---|---|
| 4,216,766 A | 8/1980 | Duykers et al. | |
| 4,497,313 A | 2/1985 | Kurosawa | |
| 4,793,352 A | 12/1988 | Eichenlaub | |
| 4,880,415 A | 11/1989 | Urakami | |
| 5,069,208 A | 12/1991 | Noppel et al. | |
| 5,241,958 A * | 9/1993 | Noeldner | 607/86 |
| 5,674,268 A | 10/1997 | Riazi | |
| 6,053,649 A | 4/2000 | Ronai | |
| 6,393,633 B2 | 5/2002 | Ferber | |

* cited by examiner

*Primary Examiner* — Aaron Roane
(74) *Attorney, Agent, or Firm* — Jerry Fong

(57) ABSTRACT

A therapeutic apparatus for providing therapeutic benefits to an immersed body part due to contact with a heated or unheated homogenous medium. The therapeutic apparatus includes at least two vibration generators for generating two waveforms at two distinct areas of the vibratory vessel, where the two waveforms are converging on each other and combined together to create a constructive and destructive pulse waveform having a larger constructive amplitude than the amplitude of the original wave and a smaller destructive amplitude than the amplitude of the original wave for providing a constructive and destructive pulse wave massaging effect to the body part of the user immersed within the homogenous medium contained within the vibratory vessel.

15 Claims, 19 Drawing Sheets

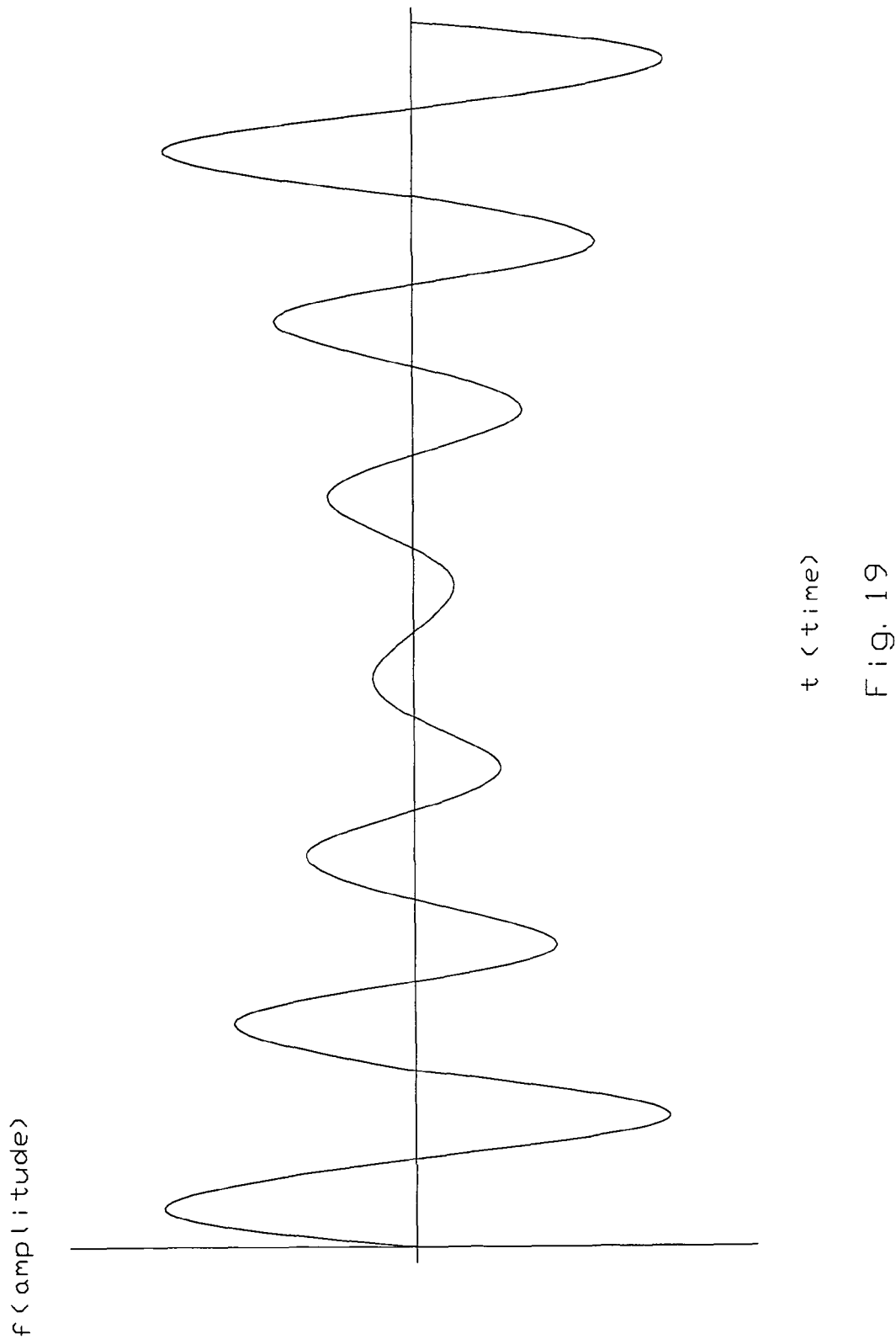

US 8,216,291 B1

APPARATUS AND METHOD OF PROVIDING THERAPEUTIC IMMERSIVE, VIBRATORY AND HEAT TREATMENT TO A BODY PART

This application is a continuation-in-part of application Ser. No. 09/962,464 filed on Sep. 25, 2001, now pending.

BACKGROUND OF THE INVENTION

1. Field of the Invention

The present invention relates generally to the field of therapeutic devices. More particularly, the present invention relates to an apparatus and method of applying a contained homogenous medium in combination with non-turbulent flow waves traveling through the homogenous medium to an immersed body part. In particular, the present invention relates to an apparatus and method for the application of therapeutic heat and enhanced permeability of a homogenous medium and additives to a body part.

2. Description of the Prior Art

Specifically, electric wax warmer devices are well known in the art. These devices convert a homogenous wax medium from a semi-solid to a fluid state and permit immersion of a body part for both therapeutic heat and cosmetic benefits. One of the disadvantages with prior art wax warmer devices is that they only have a heating means for raising and maintaining the temperature of the homogenous wax medium. None of the prior art devices have means for generating non-turbulent flow waves within the container such that the waves travel through the heated homogeneous wax medium and onto the body part for providing both a massaging effect and enhanced permeability. Another disadvantage with prior art devices is that they do not provide for continuous exposure to a homogenous medium, its additives or heat.

U.S. Pat. No. 4,793,352 issued to Eichenlaub on Dec. 27, 1988 for "Limited Heat Transfer Device And Method" discloses a limited heat transfer device and method for transferring heat to another object with close regulation of the maximum temperature obtainable. It comprises a vaporization unit wherein heat transfer material is vaporized. Vapors are then directed to terminals where heat transfer is controlled through condensation heat loss. Terminals have devices for removing excess earwax, providing physical therapy to body extremities and industrial, high temperature applications such as plastic welding.

U.S. Pat. No. 5,069,208 issued to Noppel et al. on Dec. 3, 1991 for "Therapeutic Device Comprising A Mass Of A Thermally Active Material" discloses a therapeutic device comprising a mass of a thermally active material. It comprises a pad for hot or cold therapeutic applications. The pad has a fluid-tight and flexible covering that may be of a double or triple composite sheet. There is provided a mass of heat-exchanging fluid which may be a gel, an emulsion, or another stable fluid which is enclosed in the covering.

U.S. Pat. No. 5,674,268 issued to Riazi on Oct. 7, 1997 for "Method For Providing Therapeutic Heat Treatment And Kit For Practice Thereof" discloses an apparatus and method for providing therapeutic heat treatment. The method comprises the steps of placing a suitable fluid in a container; placing wax in the container; heating the combination of the wax and the fluid until the wax has melted forming a layer and the fluid has reached the treatment temperature; and passing the body part through the layer of wax and into the fluid to form a glove around the body part.

U.S. Pat. No. 6,053,649 issued to Ronai on Apr. 25, 2000 for "Wax Warmer And Applicator Apparatus" discloses a wax warmer and applicator apparatus for heating and applying a depilatory wax to skin for the removal of unwanted hair. It comprises an electric wax warmer and a wax applicator able to store and carry a supply of warm liquid wax from the warmer to an area of the body. A compressible handle on the applicator allows the liquid wax to be forced out of the applicator and spread onto the skin in a very thin layer. The applicator is automatically refilled when placed back into the wax warmer and the compressible handle is released.

U.S. Pat. No. 4,216,766 issued to Duykers et al. on Aug. 12, 1980 for "Treatment Of Body Tissue By Means Of Internal Cavity Resonance" discloses a method and apparatus for treatment of tissue located in a specified region of a mammal. The region being proximate to a gas filled cavity that is contained in a fluid medium within the animal. The method comprises the steps of determining the resonance frequency of the cavity, and directing an acoustic signal upon the cavity to resonate it at a selected level of intensity until a first phase of the treatment has been concluded. Vessel contains a transducer that is capable of projecting an acoustic signal into medium, where the signal is determined by a control device coupled to the transducer. This patent only utilizes one transducer to generate acoustic signals having frequencies in a range of 20 KHz to 30 KHz.

U.S. Pat. No. 6,393,633 issued to Ferber on May 28, 2002 for "Bath Apparatus" discloses an apparatus is provided for bathing body parts, such as the feet. The apparatus includes a bath chamber for containing fluid, such as water, and receiving the body part therein. The bath chamber includes a bottom surface and a wall structure extending upwardly therefrom. A pump is disposed adjacent to the bottom surface of the bath chamber, and a bubble egress tube is provided in communication with the pump and the bath chamber bottom surface. The bubble egress tube has a continuous configuration which traverses a surface area of the bath chamber bottom surface having a width dimension greater than the width of the egress tube. Air from the pump is directed into the bath chamber through egress holes formed in the bubble egress tube, thereby generating air bubbles in the fluid contained in the bath chamber. The wall structure includes a contact area adapted to be uncovered by fluid contained in the bath chamber. A heating member is provided on the contact area for providing heat to the body part when the body part is placed on the contact area. In addition, a heater is provided in communication with the bath chamber for maintaining the heat of the fluid contained therein. Furthermore, the bath apparatus includes a vibration assembly in communication with the bath chamber for imparting vibration to the bath chamber. The vibration assembly includes a motor affixed to an underside of the bath chamber, an output shaft rotatable driven by the motor, and a counterweight affixed to the output shaft. This patent utilizes one vibration generator and does not combine two waveforms at two distinct areas, where the two original waveforms are converging on each other to combine together to create a constructive and destructive pulse waveform from the two original waveforms. It further does not disclose using homogeneous wax medium as a medium for the bath apparatus nor does it maintains the medium within a temperature range of 85° F. to 115° F.

U.S. Pat. No. 4,880,415 issued to Urakami on Nov. 14, 1989 for "Warm Bath For Hands And Feet" discloses a bath apparatus for simultaneously soaking the hands and feet in a bathing agent consisting mainly of wax. It includes an upper and lower container each containing the bathing agent. The bottom wall and peripheral sidewall of each container comprises a base structure and an inner layer on the base structure, the inner layer being made of a corrosion-resistant material. The base structure has a bottom outer surface juxtaposed to the bottom wall and a side outer surface juxtaposed to the sidewall. A first electric heater is provided on the bottom outer surface and a second electric heater is provided on the side outer surface. A temperature sensor for detecting the temperature of the bathing agent is provided in each of the containers, and a temperature control is operable connected between the temperature sensor and the first and second electric heaters for controlling the temperature of the bathing agent in each of the containers, whereby the entire volume of the bathing agent in each of the upper and lower containers is uniformly heated by the first and second electric heaters and the temperature of the bathing agent in the upper and lower containers is maintained substantially even at all locations in the respective container by the first and second electric heaters.

It is desirable to provide an apparatus and method of generating non-turbulent flow waves within a container such that the waves travel through a heated or non-heated homogenous wax medium onto a body part for providing both a massaging effect and enhanced permeability in addition to heat treatment.

SUMMARY OF THE INVENTION

The present invention is an apparatus and method of providing therapeutic benefits to a body part due to contact with a homogenous medium and periodic disturbances of that medium. The apparatus provides for containment of a homogenous medium, exposure of the top surface of the homogenous medium to permit the inclusion of a body part, and creation of non-turbulent flow periodic disturbances that travel through the homogenous medium. In addition, the apparatus and method also provides for therapeutic heat benefits in combination with the vibrating homogenous medium to a body part with subsequent enhanced permeability.

It has been discovered, according to the present invention, that by providing an apparatus and method with therapeutic benefits wherein a homogenous medium surrounds and massages a body part, then an improved therapeutic massager is created with enhanced permeability for cosmetic benefits.

It has additional been discovered, according to the present invention, that by providing an apparatus and method with therapeutic benefits wherein a homogenous medium is heated such that the heated homogenous medium surrounds and massages a body part, then an improved therapeutic heated massager is created with enhanced permeability for cosmetic benefits.

It has further been discovered, according to the present invention, that by providing an apparatus and method with therapeutic benefits wherein a homogenous medium is heated and vibrated onto a body part, then an improved therapeutic heated massager as well as a multiple frequency massager is created with enhanced permeability for cosmetic benefits.

It is an object of the present invention to provide an apparatus and method with therapeutic benefits, where a homogenous medium surrounds and massages a body part so that an improved therapeutic massager is created.

It is also an object of the present invention to provide an apparatus and method with therapeutic benefits, where a homogenous medium is heated and surrounds a body part to be massaged, so that an improved therapeutic heated massager is created with enhanced permeability for cosmetic benefits.

It is an additional object of the present invention to provide an apparatus and method with therapeutic benefit, where a homogenous medium is heated and shake onto a body part so that an improved therapeutic heated multiple frequency massager is created with enhanced permeability for cosmetic benefits.

It is a further object of the present invention to provide an apparatus with a heating means so that the retained suitable homogenous medium is heated to and maintained at a predetermined selected temperature range.

It is still a further object of the present invention to provide an apparatus with at least two periodic force means which are attached so that a suitable homogenous medium is disturbed by complex variable frequency waves due to high amplitude plate vibrations.

Described briefly, the present invention is an apparatus and method of applying a heated or unheated homogenous medium to a body part of a user as well as generating shaking through the heated homogenous medium to vary the massaging effect created by the shaking. The present invention apparatus comprises a container for retaining a suitable homogenous medium therein. The container has an exposure top surface so that the homogenous medium is accessible by the body part of the user and means for generating traveling waves within the homogenous medium from high amplitude plate variations due to an attached periodic force means to its bottom surface.

The present invention is a therapeutic apparatus for providing therapeutic benefits to a body part of a user using the apparatus. Described generally, the body part of the user is immersed within a combination of homogenous wax medium and mineral oil contained within the vibratory vessel of the therapeutic apparatus. Therapeutic apparatus includes at least two vibration generators for generating two waveforms at two distinct areas of the vibratory vessel, where the waveforms are converging on each other to be combine together to create a constructive and destructive pulse waveform having a larger constructive amplitude than original waveforms and a smaller destructive amplitude than the amplitude of the original waveforms for providing a constructive and destructive pulse wave massaging effect to the body part of the user immersed within combination of the homogenous wax medium and mineral oil contained within the vibratory vessel.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 19 is an illustrative diagram showing a constructive and destructive pulse wave pattern of the combined two non-turbulent traveling waves, rising wave (constructive) and falling wave (destructive).

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Described briefly, the present invention is an apparatus and method of providing therapeutic benefits to a body part due to contact with a homogenous medium and periodic disturbances of that medium. The apparatus provides for containment of a homogenous medium, exposure of the top surface of the homogenous medium to permit the inclusion of a body part, and creation of non-turbulent flow periodic disturbances that travel through the homogenous medium. In addition, the apparatus and method also provides for therapeutic heat benefits in combination with the vibrating homogenous medium to a body part with subsequent enhanced permeability.

Figure 1:
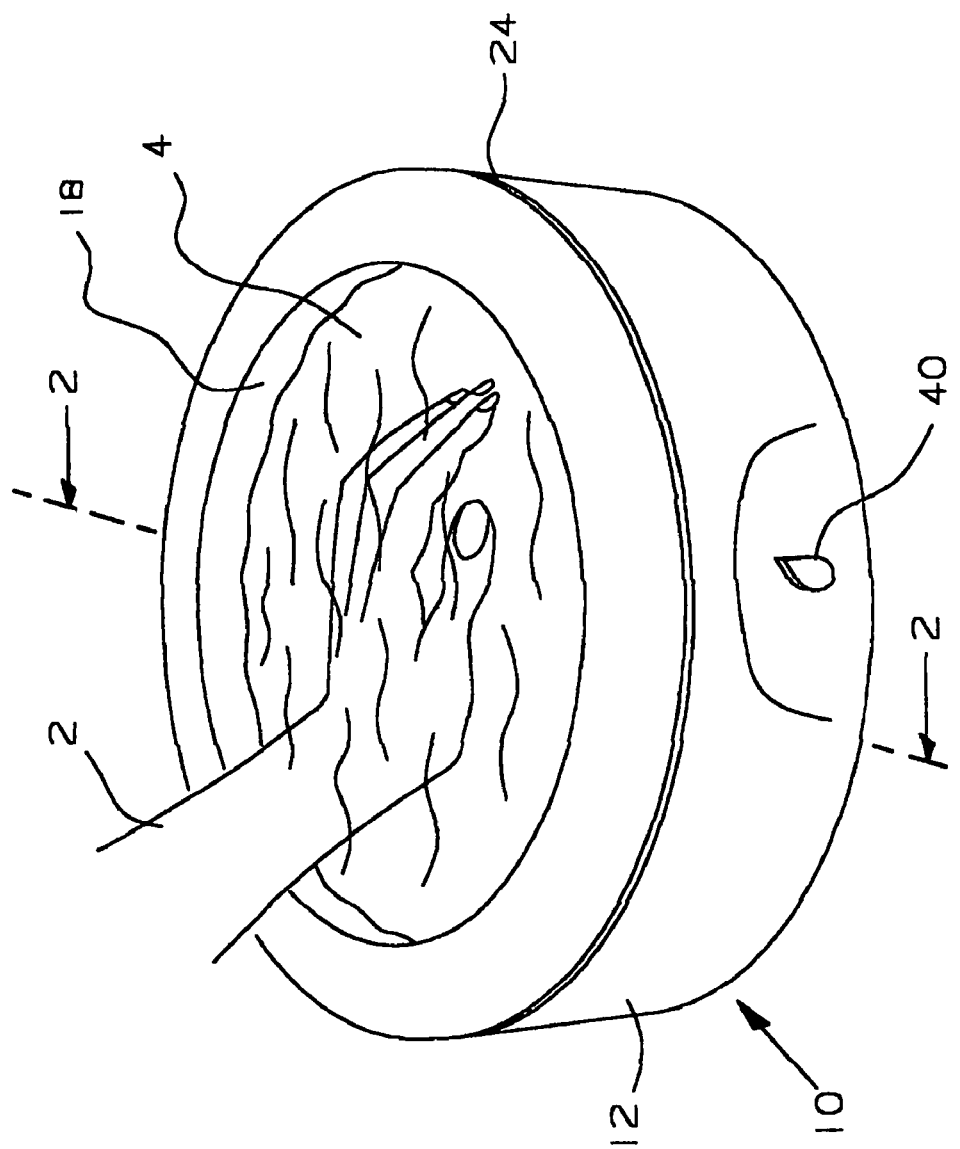
FIG. 1 is a perspective view of a preferred embodiment of the present invention medium warmer massage apparatus, showing a body part covered by a homogenous medium which is combined with traveling waves.
Figure 2:
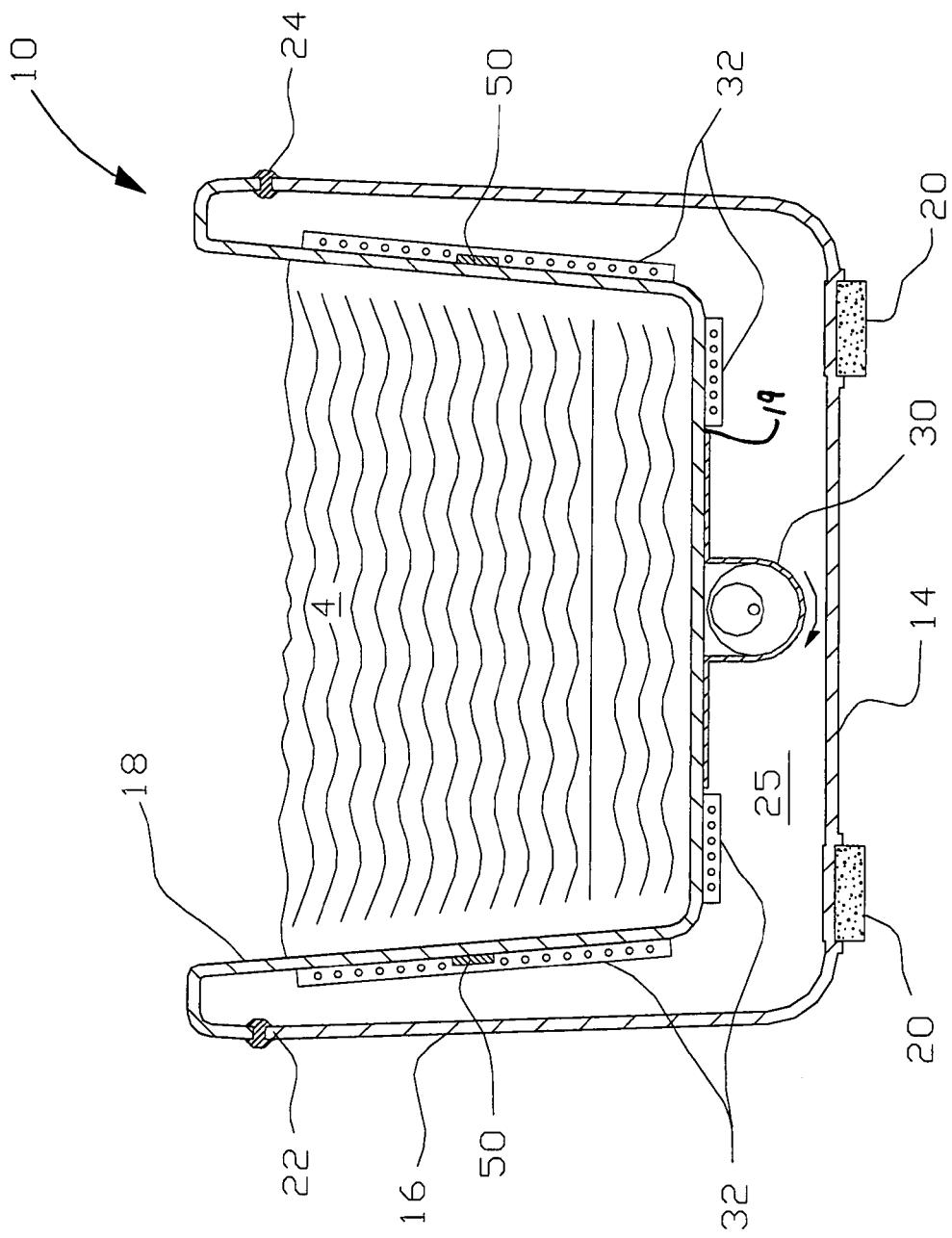
FIG. 2 is a cross-sectional view taken along lines 2-2 of FIG. 1.
Figure 3:
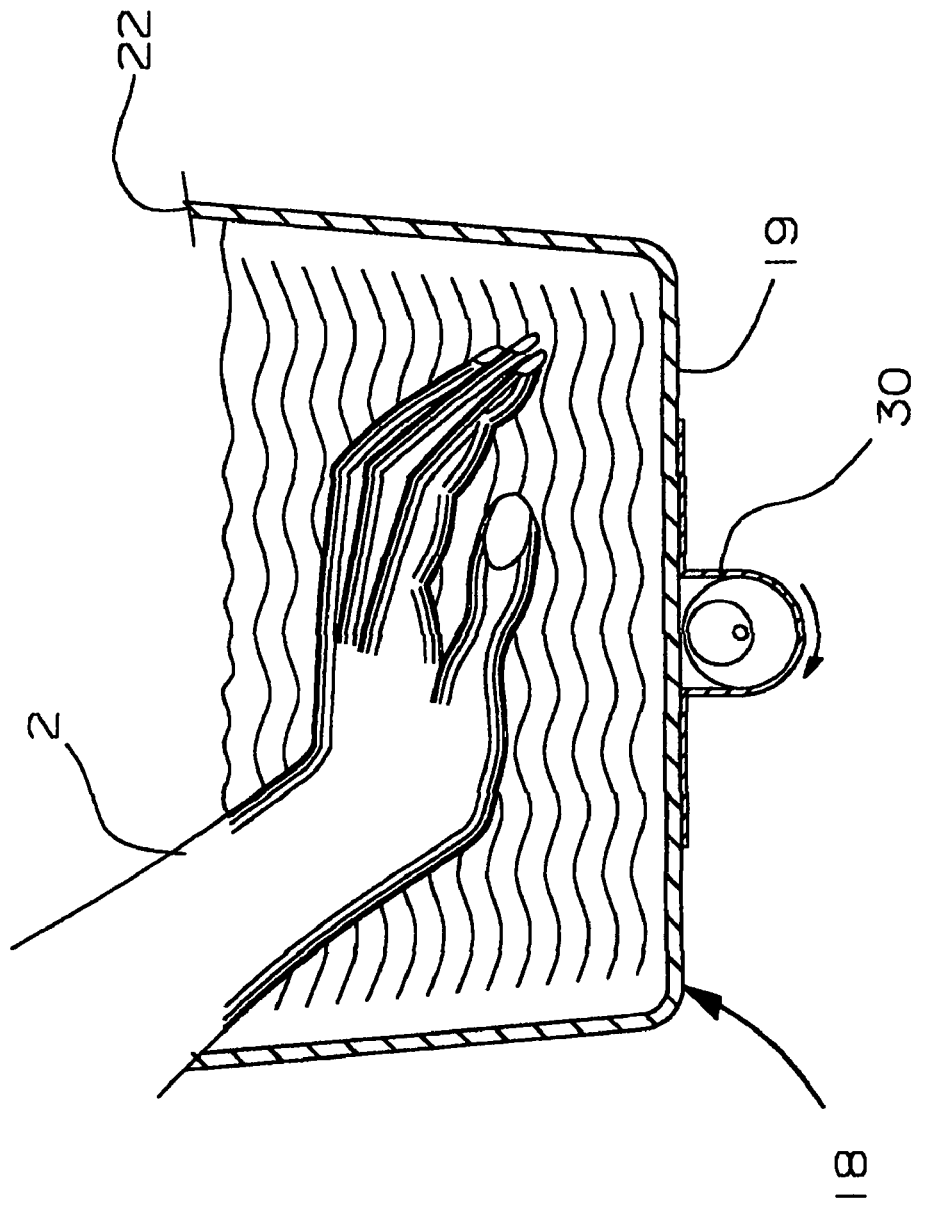
FIG. 3 is a cross-sectional view showing the container without the outer cabinet in accordance with the present invention.

Referring to FIGS. 1, 2 and 3, there is shown at 10 a preferred embodiment of the present invention apparatus and method of providing therapeutic immersive, vibratory and heat treatment to a body part such as a hand. The apparatus and method is for applying a heated homogenous medium 4 to a body part 2 of a user as well as generating vibrations through the heated homogenous medium 4 and onto the body part 2 of the user to vary the massaging effect created by the vibrations.

For clarity purposes in these figures, electrical wiring are not illustrated, but are conventional in the art and would be easily accomplished by persons skilled in the art.

The apparatus 10 comprises a hollow cabinet 12 that is constructed from plastic material, metal material or any other suitable material. The cabinet 12 has a bottom wall 14 and a circumferential sidewall 16 which extends upwardly from the bottom wall 14 to form an upper lip 22 for retaining and securing a ledge 24 of a vessel or container 18. There are provided rubber or sponge pads 20 that are affixed to the exterior surface of the bottom wall 14 of the cabinet 12 for providing stationary means so that the apparatus 10 does not slip or move when placed on a table, floor or supporting means. The container 18 is spaced apart from the bottom wall 14 of the cabinet 12 to form a chamber 25 as shown in FIG. 2.

The apparatus 10 further comprises at least one vibration generator or oscillation generator 30 and one or more heating means 32. The at least one vibration generator 30 is centrally located and affixed to the exterior surface of the bottom 19 of the container 18 and is concealed within the chamber 25 between the container 18 and the cabinet 12. The at least one vibration generator 30 may include magnetic means, eccentric motors, solenoids, transducers, sonic transducers, vibratory means or any other suitable means known to one skilled in the art for providing vibration or shaking movements of the container which in turn moves the homogenous medium contained within the container.

Figure 13:
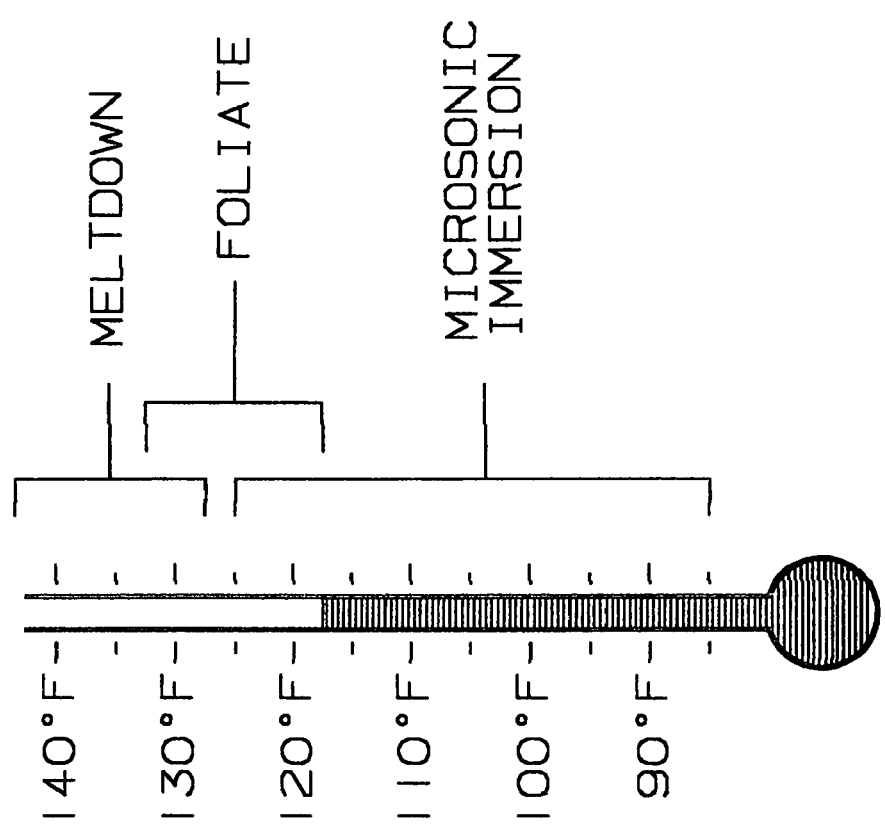
FIG. 13 is a graph indicating a temperature scale in relationship to the usage of a suitable homogenous wax medium with mineral oil additives in accordance with the present invention.

The at least one vibration generator 30 can be operated between a frequency of 400 Hz to 10 kHz. The heating means 32 may include heating plates or other suitable means known in the art. Heating means 32 are located on opposite sides of the vibration generator 30 and the exterior surface of the sidewall of the container. The heating means 32 can heat a homogenous medium or it can melt a semi-solid wax medium contained within the container 18. The heating means 32 can heat the homogenous wax medium 4 to a temperature range of 125° F. to 145° F. (see FIG. 13) so that the semi-solid wax can be melted into a hot homogenous wax medium 4. Once the semi-solid wax has been melted down, the heating means 32 are set at a temperature range of 85° F. to 125° F. so that the body part 2 of the user can immerse into the heated homogenous wax medium 4.

The apparatus 10 may be supplied by 110V AC powered or DC powered, such as batteries and may further includes a control switch 40 or control panel which may be programmable microprocessor for automatically controlling the operation of the apparatus 10. The control panel 40 may be electrically coupled to a control circuitry (not shown) that controls the vibration generator 30, heating means 32 and temperature sensors 50. The temperature sensors 50 are affixed to the sidewall of the container 18 for sensing temperature of the heated homogenous wax medium 4 contained within the container 18. The control circuitry may include a microprocessor that may be electrically coupled between a relay and the temperature sensors. The relay may be coupled to the power supply and the heating means 32. The user can immerse his or her body part into the heated homogenous wax medium between the temperatures of 85° F. to 125° F. such that the body part 2 is provided with a therapeutic heated homogenous wax medium treatment as well as a massaging treatment to vary the sensation felt by the body part of the user contained within the container 18.

Figure 4:
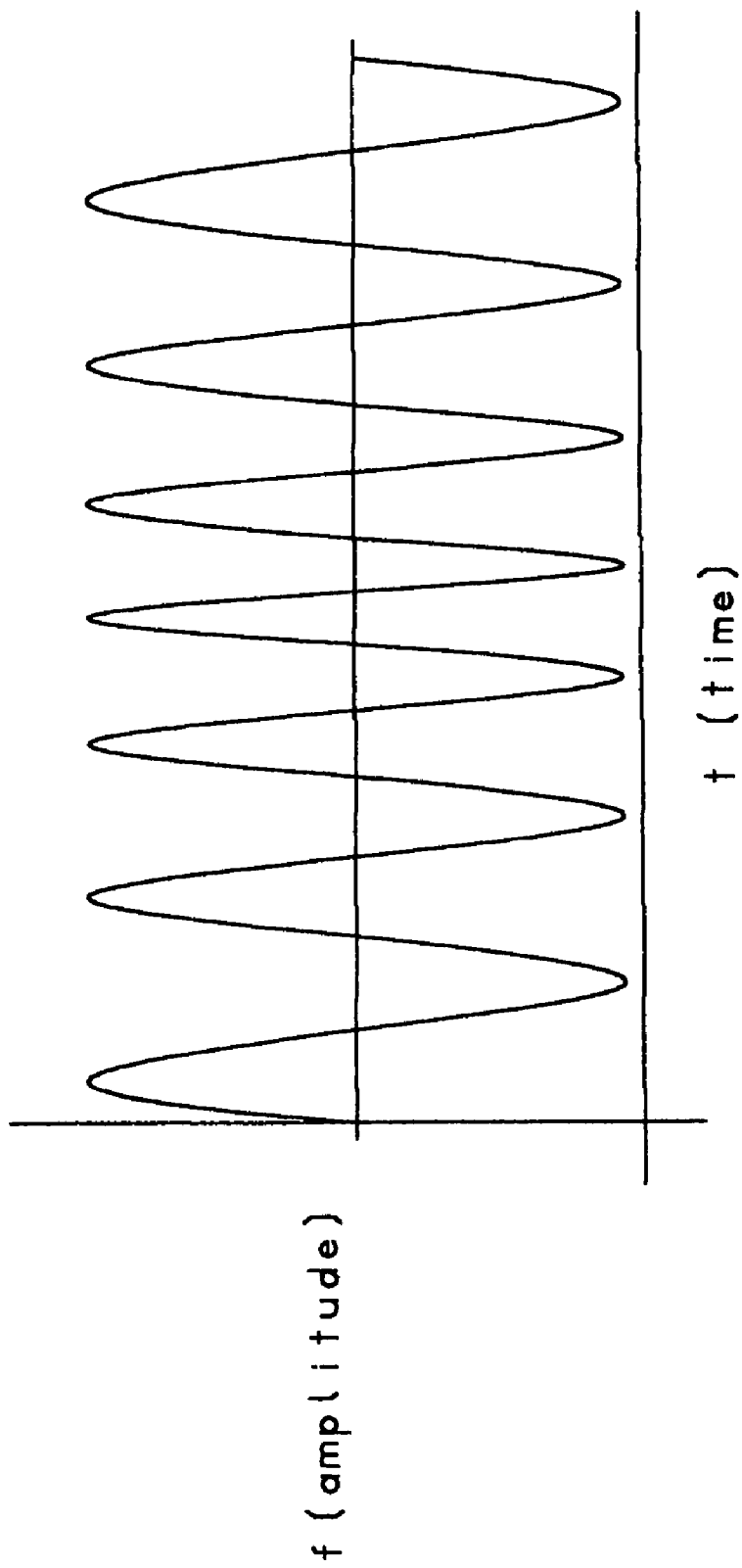
FIG. 4 is a graph showing a traveling wave oscillation vibrating harmonically with the period of a periodic force means varying in frequency.

Referring to FIG. 4, there is shown a graph showing a traveling oscillation wave vibrating harmonically with the period of a periodic force means 30 varying in frequency.

Figure 5:
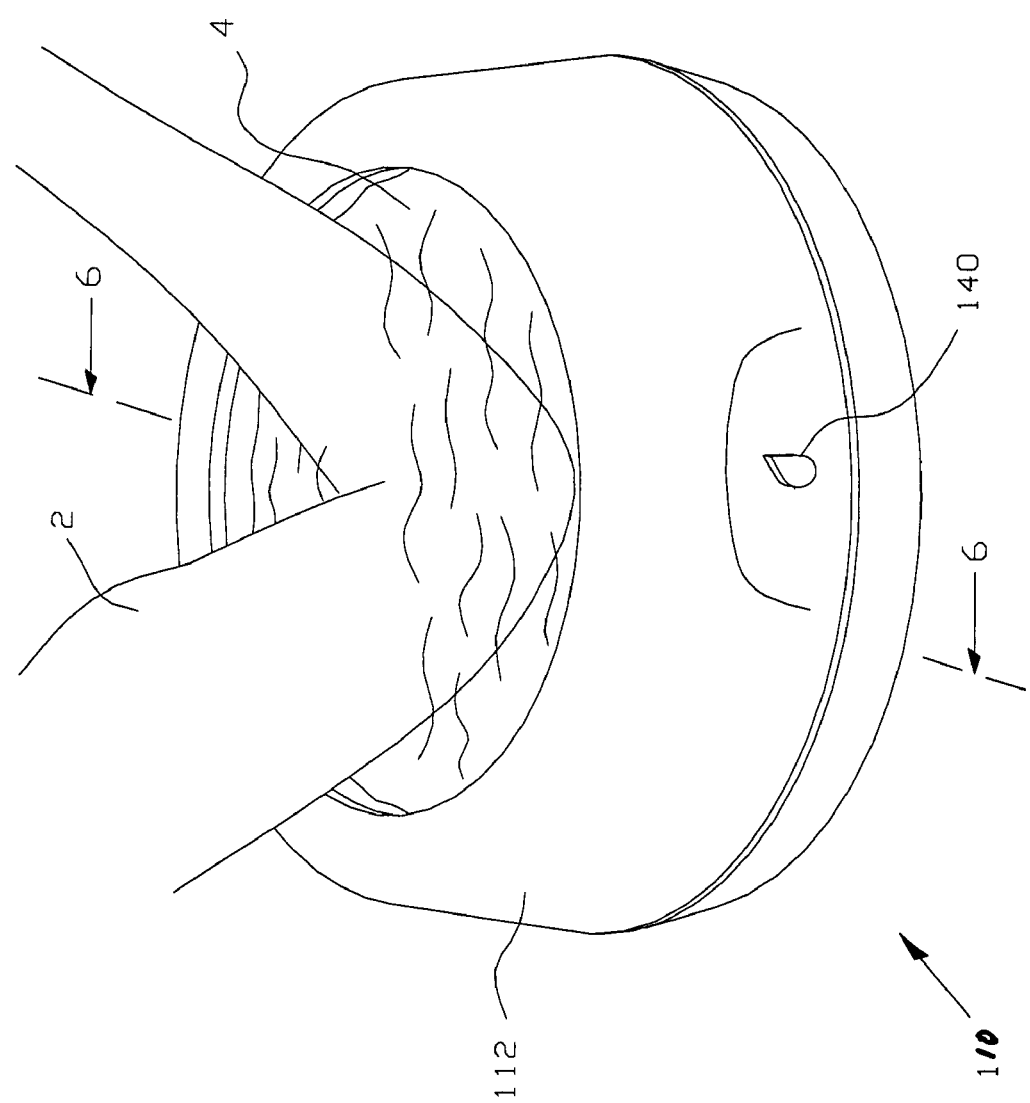
FIG. 5 is a perspective view of an alternative embodiment of the present invention complex wave medium warmer massage apparatus, showing a body part covered by a homogenous medium which is combined with traveling waves varying in both frequency and amplitude.
Figure 6:
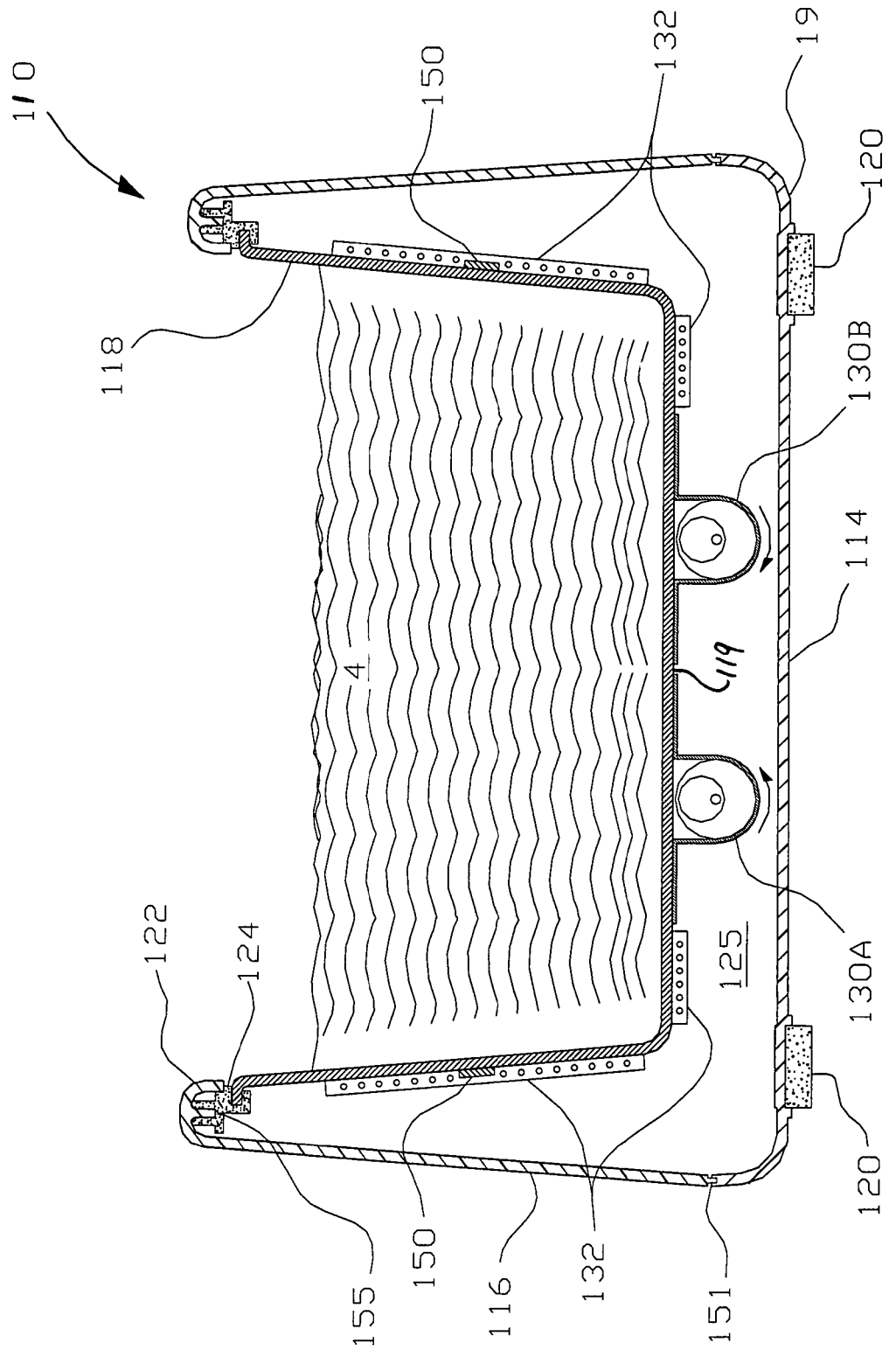
FIG. 6 is a cross-sectional view taken along lines 6-6 of FIG. 5.
Figure 7:
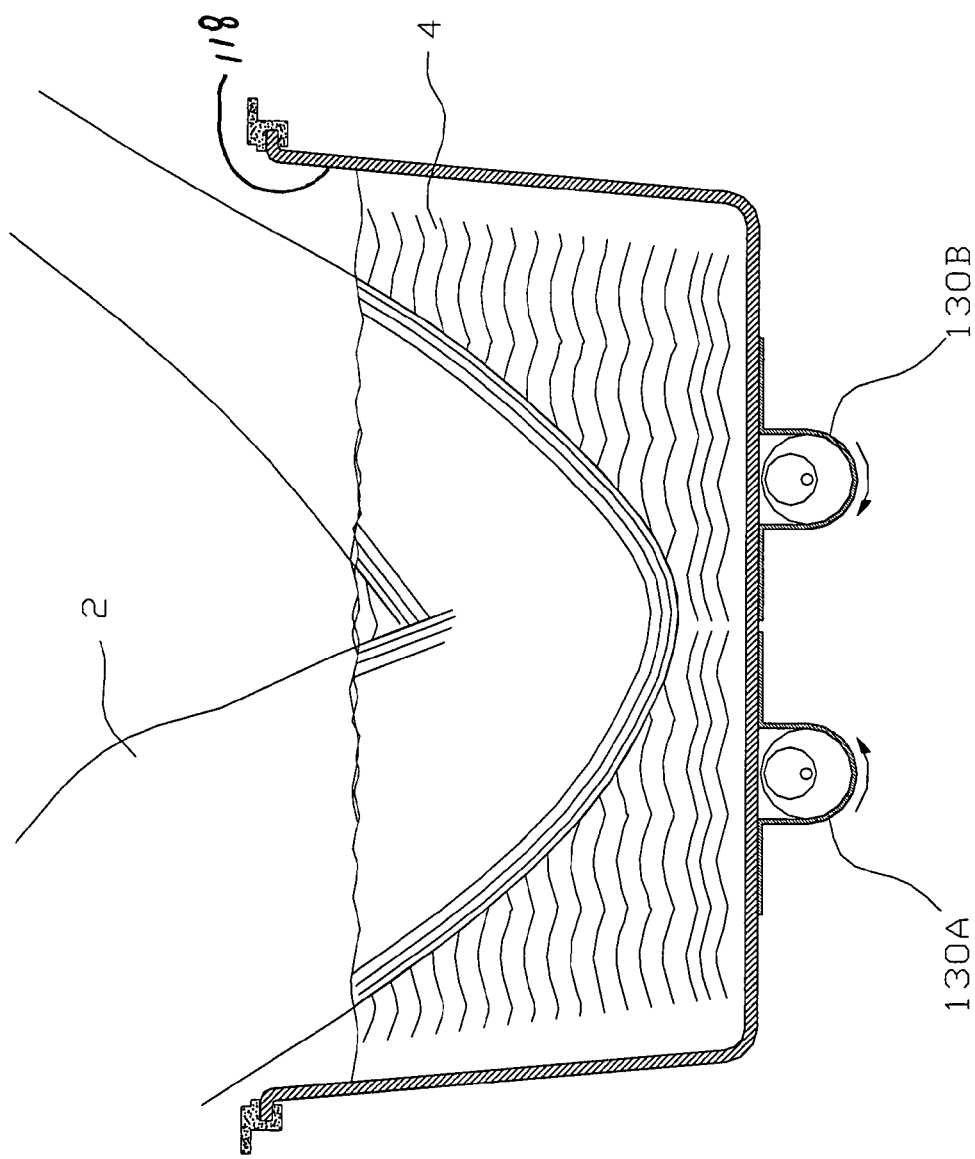
FIG. 7 is a cross-sectional view showing the container without the outer cabinet in accordance with the present invention shown in FIG. 6.

Referring to FIGS. 5, 6 and 7, there is shown at 110 an alternative embodiment of the present invention apparatus of providing therapeutic immersive, vibratory and heat treatment to a body part such as an elbow. The apparatus and method 110 is used for applying a heated homogenous medium 4 to a body part 2 of a user as well as generating vibrations through the heated homogenous medium 4 and onto the body part 2 of the user to vary the massaging effect created by the vibrations.

This alternative embodiment of the present invention is very similar to the preferred embodiment just discussed above and the only difference is the nature and configuration of the vibration generators 130. All of the identical parts of this embodiment of the present invention medium warmer massage apparatus 110 are numbered correspondingly with 100 added to each number.

For clarity purposes in these figures, electrical wiring are not illustrated, but are conventional in the art and would be easily accomplished by persons skilled in the art.

The apparatus 110 comprises a hollow cabinet 112 that is constructed from plastic material, metal material or any other suitable material. The cabinet 112 has a bottom wall 114 and a circumferential sidewall 116 which extends upwardly from the bottom wall 114 to form an upper lip 122 and opening for retaining and securing a ledge 124 of a vessel or container 118. The retaining and securing means includes a locking mechanism 155 as shown in FIG. 6. In this embodiment of the hollow cabinet 112, the circumferential sidewall 116 may be connected to the bottom wall 114 by press-fitted pegs or posts 151 (see FIG. 6).

There are provided rubber or sponge pads 120 that are affixed to the exterior surface of the bottom wall 114 of the cabinet 112 for providing stationary means so that the apparatus 110 does not slip or move when placed on a table, floor or supporting means. The container 118 is spaced apart from the bottom wall 114 of the cabinet 112 to form a chamber 125 as shown in FIG. 6.

The apparatus 110 further comprises at least two vibration or oscillation generators 130A, 130B and one or more heating means 132. The at least two vibration generators 130A and 130B are located at two distinct locations and affixed to the exterior surface of the bottom 119 of the container 118 and are concealed within the chamber 125 between the container 118 and cabinet 112. According to the present invention, when there is a distribution of resonant modes of a first oscillation wave 130A over one area and there is another distribution of resonant modes of a second oscillation wave 130B over another area, then there will be a distribution of resonant modes of a third oscillation wave 135 which is the combination of the first and second oscillation waves 130A and 130B.

The least two vibration generators 130A and 130B may include magnetic means, eccentric motors, solenoids, transducers, sonic transducers, vibratory means or any other suitable means known to one skilled in the art for providing vibration or shaking movements to the homogenous medium. The at least two vibration generators 130A and 130B can be operated between a frequency of 400 Hz to 10 kHz. The heating means 132 may include plates or other suitable means known in the art. Heating means 132 are located on the bottom 119 and the exterior surface of the sidewall of the container 118. The heating means 132 can heat a homogenous medium or it can melt a semi-solid wax medium contained within the container 118. The heating means 132 can heat the homogenous wax medium 4 to a temperature range of 125° F. to 145° F. (see FIG. 13) so that the semi-solid wax can be melted into a hot homogenous wax medium 4. Once the semi-solid wax has been melted down, the heating means 132 can be set at a temperature range of 85° F. to 125° F. so that the body part 2 of the user can immerse into the heated homogenous wax medium 4.

The apparatus 110 may be supplied by 110V AC powered or DC powered, such as batteries and may further includes a control switch 140 or control panel which may be programmable microprocessor for automatically controlling the operation of the apparatus 110. The control panel 140 may be electrically coupled to a control circuitry that controls the vibration generators 130A and 130B, heating means 132 and temperature sensors 150. The temperature sensors 150 are affixed to the sidewall of the container 118 for sensing temperature of the heated homogenous wax medium 4 contained within the container 118. The control circuitry may include a microprocessor that may be electrically coupled between a relay and the temperature sensors. The relay may be coupled to the power supply and the heating means 132. The user can immerse his or her body part into the heated homogenous wax medium between the temperatures of 85° F. to 125° F. such that the body part 2 is provided with a therapeutic heated homogenous wax medium treatment as well as a massaging treatment to vary the sensation felt by the body part of the user contained within the container 118.

Figure 8:
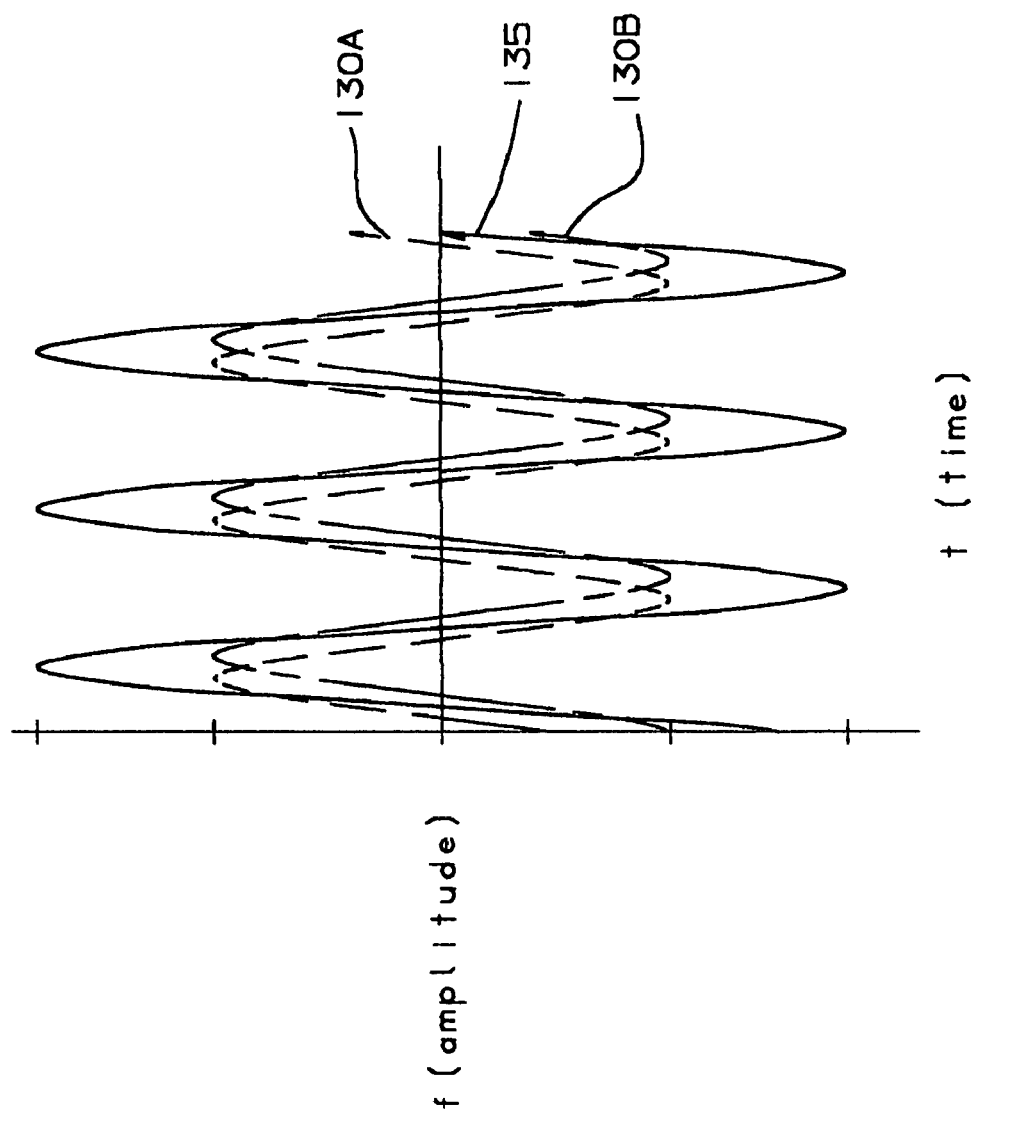
FIG. 8 is a graph showing traveling oscillation waves vibrating and varying both constructively and destructively in both frequency and amplitude with the interference of differing periods of two periodic force means to create a beat pattern in accordance with the present invention.

Referring to FIG. 8, there is shown a graph showing a first traveling oscillation wave 130A vibrating at a specific frequency, a second traveling oscillation wave 130B vibrating at a second specific frequency and a third traveling oscillation wave 135 which is the combination of the first and second traveling oscillation waves 130A and 130B. The two smaller traveling oscillation waves are in a constructive harmony, where the two waves create larger amplitude of the harmony.

Figure 9:
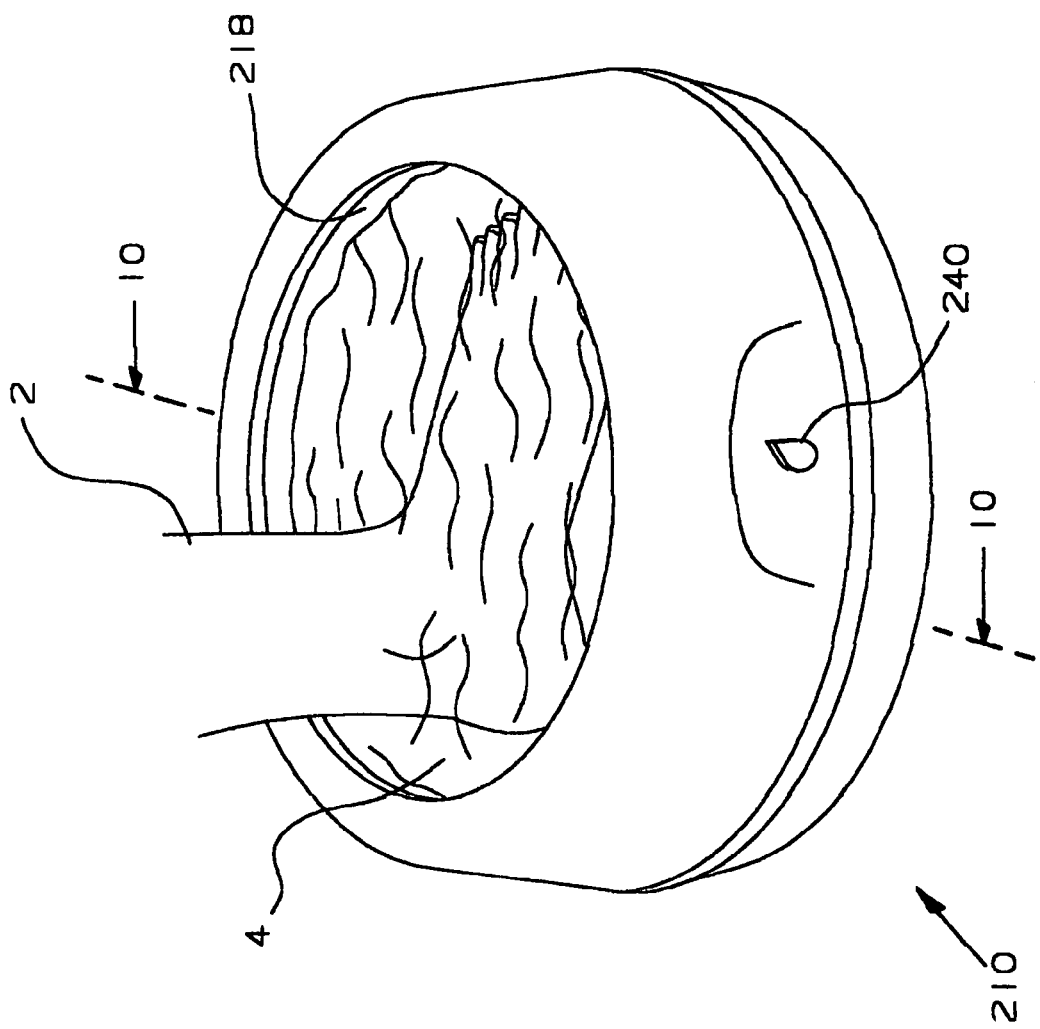
FIG. 9 is a perspective view of another alternative embodiment of the present invention medium warmer massage apparatus.
Figure 10:
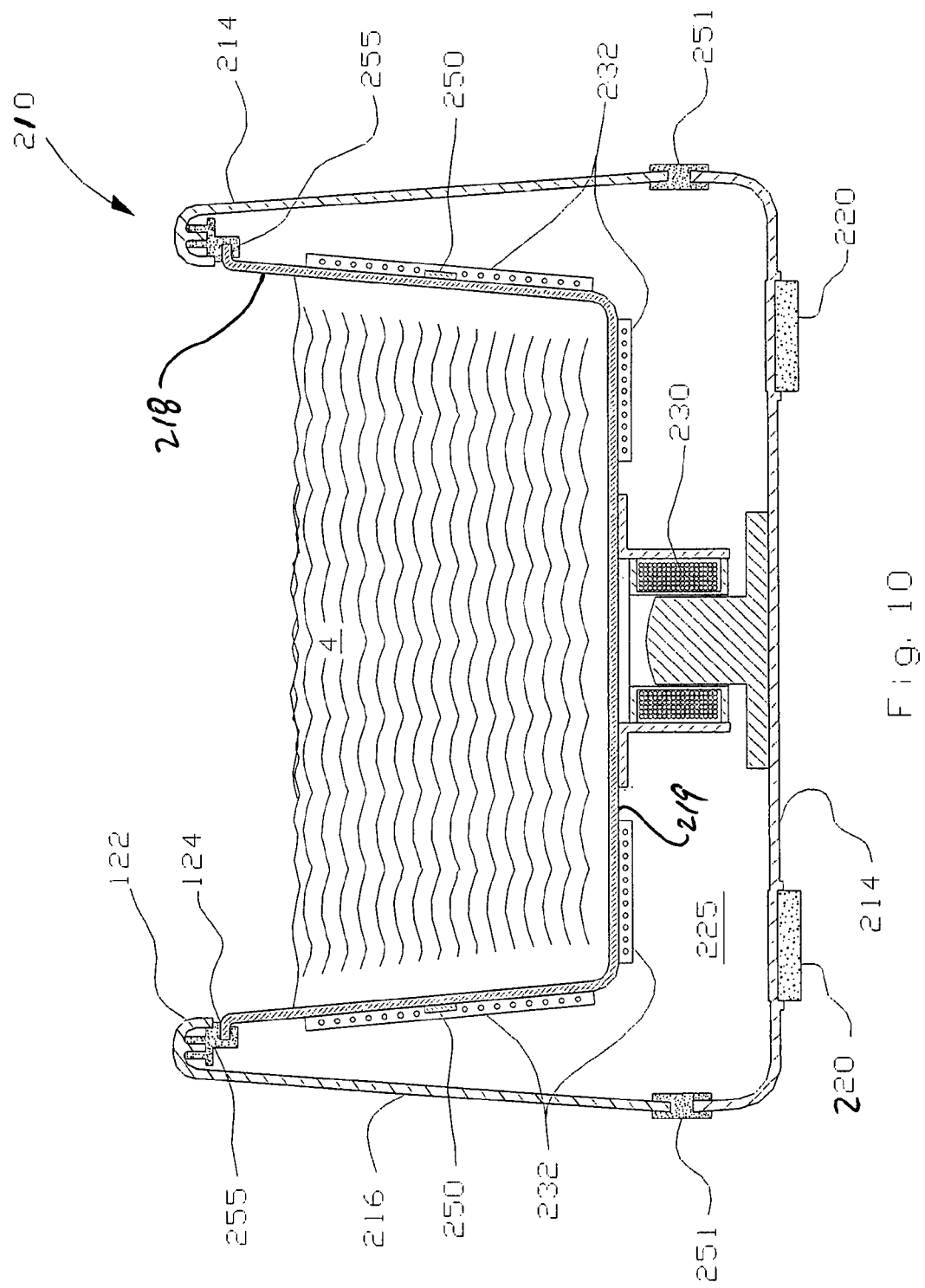
FIG. 10 is a cross-sectional view taken along the line 10-10 of FIG. 9.
Figure 11:
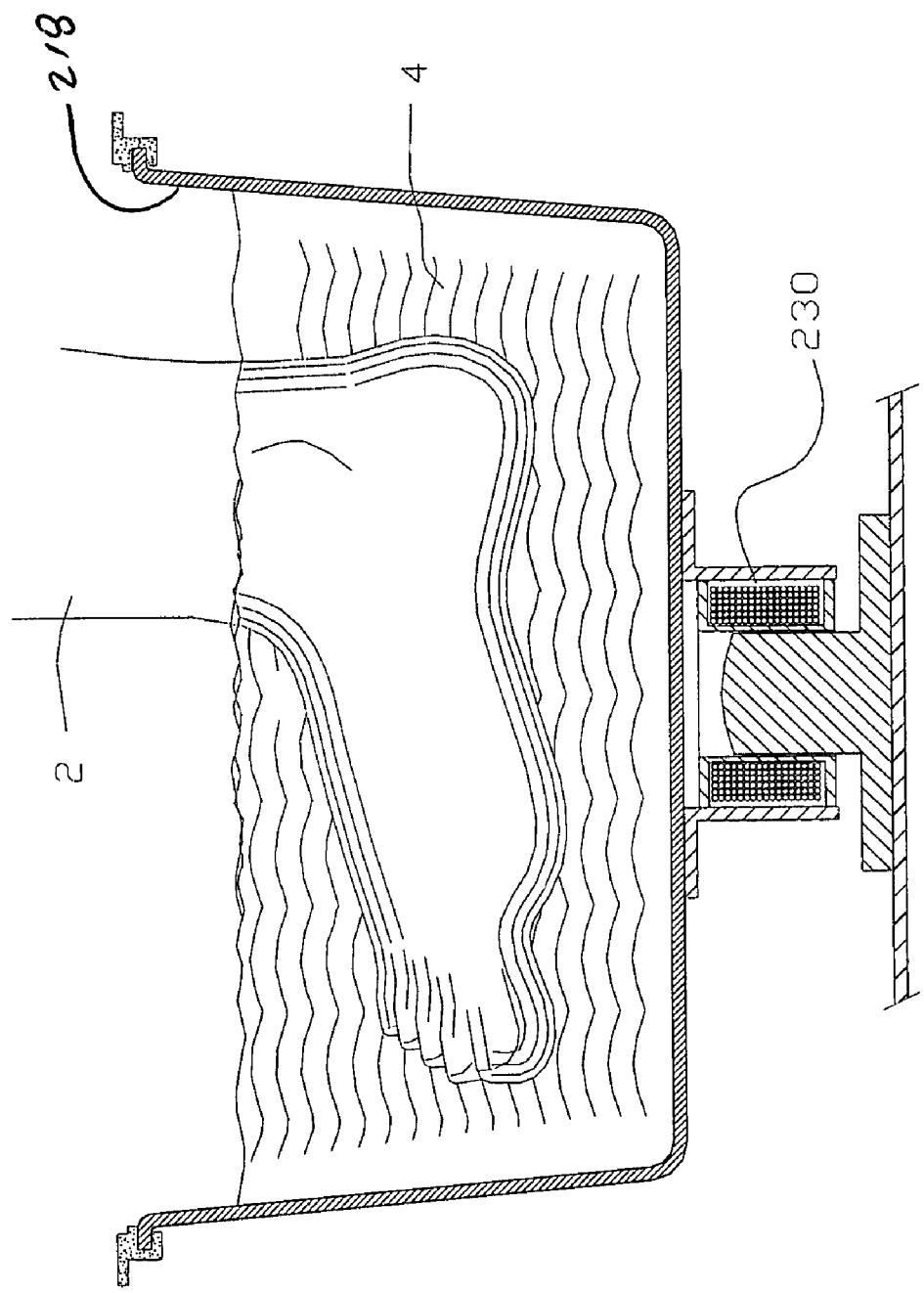
FIG. 11 is a cross-sectional view showing the container without the outer cabinet in accordance with the present invention shown in FIG. 10.

Referring to FIGS. 9, 10 and 11, there is shown at 210 an alternative embodiment of the present invention apparatus of providing therapeutic immersive, vibratory and heat treatment to a body part such as a foot. The apparatus and method 210 is used for applying a heated or unheated homogenous medium 4 to a body part 2 of a user as well as generating vibrations through the heated homogenous medium 4 and onto the body part 2 of the user to vary the massaging effect created by the vibrations.

This alternative embodiment of the present invention is very similar to the preferred embodiment just discussed above and the only difference is the nature and configuration of the vibration generator 230. All of the identical parts of this embodiment of the present invention medium warmer massage apparatus 210 are numbered correspondingly with 200 added to each number.

For clarity purposes in these figures, electrical wiring are not illustrated, but are conventional in the art and would be easily accomplished by persons skilled in the art.

The apparatus 210 comprises a hollow cabinet 212 that is constructed from plastic material, metal material or any other suitable material. The cabinet 212 has a bottom wall 214 and a circumferential sidewall 216 which extends upwardly from the bottom wall 214 to form an upper lip 122 and opening for retaining and securing a ledge 224 of a vessel or container 218. The retaining and securing means includes a locking mechanism 255 as shown in FIG. 10. In this embodiment of the hollow cabinet 212, the circumferential sidewall 216 may be connected to the bottom wall 214 by a cross-section shaped "H" attachment (see FIG. 10).

There are provided rubber or sponge pads 220 that are affixed to the exterior surface of the bottom wall 214 of the cabinet 212 for providing stationary means so that the apparatus 210 does not slip or move when placed on a table, floor or supporting means. The container 218 is spaced apart from the bottom wall 214 of the cabinet 212 to form a chamber 225 as shown in FIG. 10.

The apparatus 210 further comprises at least one vibration generator 230 and one or more heating means 232. The at least one vibration generator 230 is centrally located and affixed to the exterior surface of the bottom 219 of the container 218 and is concealed within the chamber 225 between the container 218 and cabinet 212. The least one vibration generator 230 may include magnetic means, eccentric motors, solenoids, transducers, sonic transducers, vibratory means or any other suitable means known to one skilled in the art for providing vibration or shaking movements to the homogenous medium. The at least one vibration generator 230 can be operated between a frequency of 400 Hz to 10 kHz. The at least one vibration generator 230 can be electronically controlled to have any desired amplitude or frequency or patterns and combinations.

The heating means 232 may include plates or other suitable means. Heating means 232 are located on the bottom 219 and the exterior surface of the sidewall of the container 218. The heating means 232 can heat a homogenous medium or it can melt a semi-solid wax medium contained within the container 218. The heating means 232 can heat the homogenous wax medium 4 to a temperature range of 125° F. to 145° F. (see FIG. 13) so that the semi-solid wax can be melted into a hot homogenous wax medium 4. Once the semi-solid wax has been melted down, the heating means 232 can be set at a temperature range of 95° F. to 120° F. so that the body part 2 of the user can immerse into the heated homogenous wax medium 4.

The apparatus 210 may be supplied by 110V AC powered or DC powered, such as batteries and may further includes a control switch 240 or control panel which may be programmable for automatically controlling the operation of the apparatus 110. The control panel 240 may be electrically coupled to a control circuitry (not shown) that controls the vibration generator 230, heating means 232 and temperature sensors 250. The temperature sensors 250 are affixed to the sidewall of the container 218 for sensing temperature of the heated homogenous wax medium 4 contained within the container 218.

The control circuitry may include a microprocessor that may be electrically coupled between a relay and the temperature sensors. The relay may be coupled to the power supply and the heating means 232. The user can immerse his or her body part into the heated homogenous wax medium between the temperatures of 95° F. to 120° F. such that the body part 2 is provided with a therapeutic heated homogenous wax medium treatment as well as a massaging treatment to vary the sensation felt by the body part of the user contained within the container 218.

Figure 12:
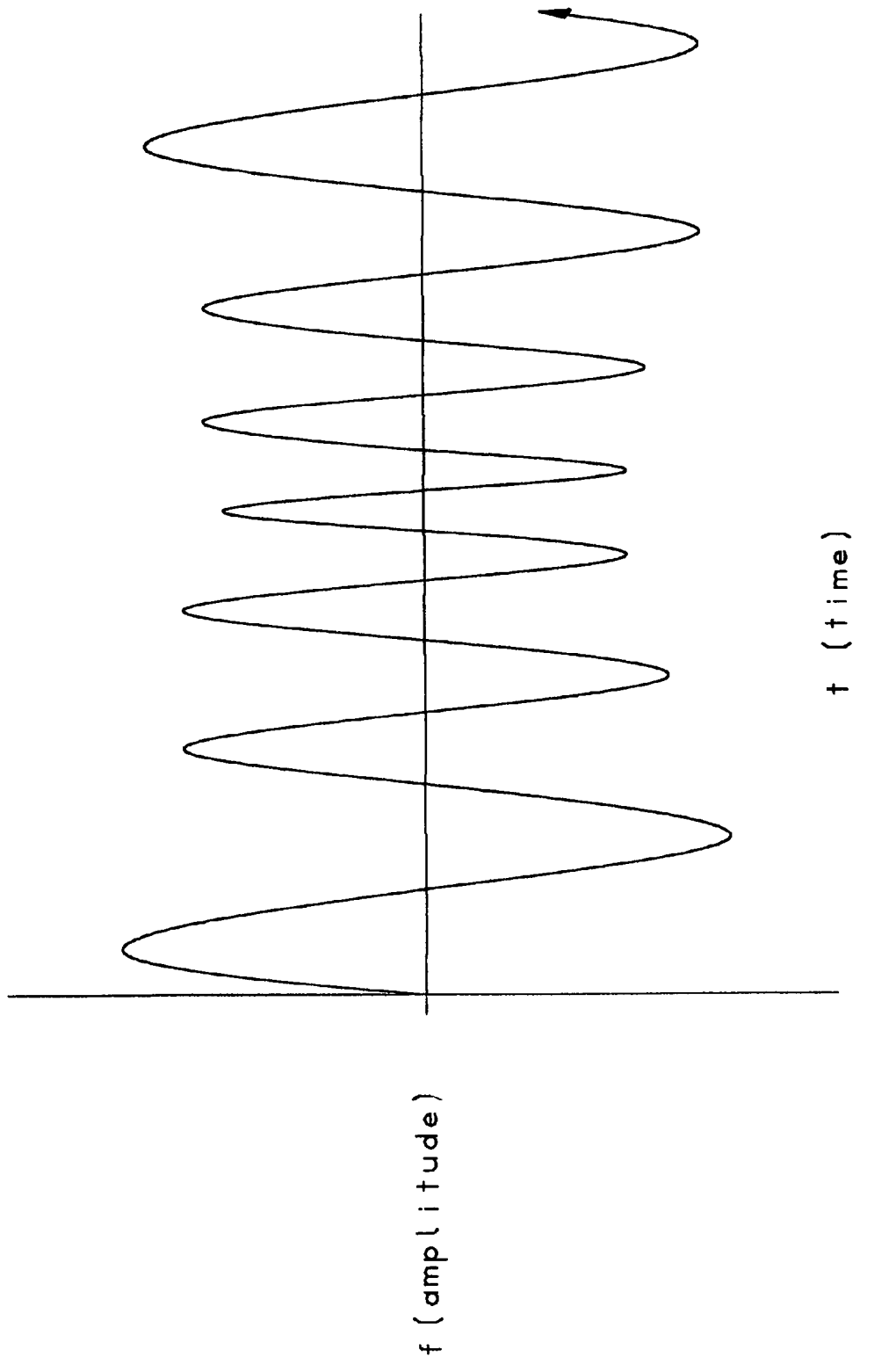
FIG. 12 is a graph showing traveling oscillation waves vibrating and varying destructively in both frequency and amplitude with the interference of differing periods of two periodic force means in accordance with the present invention.

Referring to FIG. 12, there is shown a graph showing a traveling oscillation wave vibrating at different periods of a periodic force means 230 varying in frequency.

Figure 14:
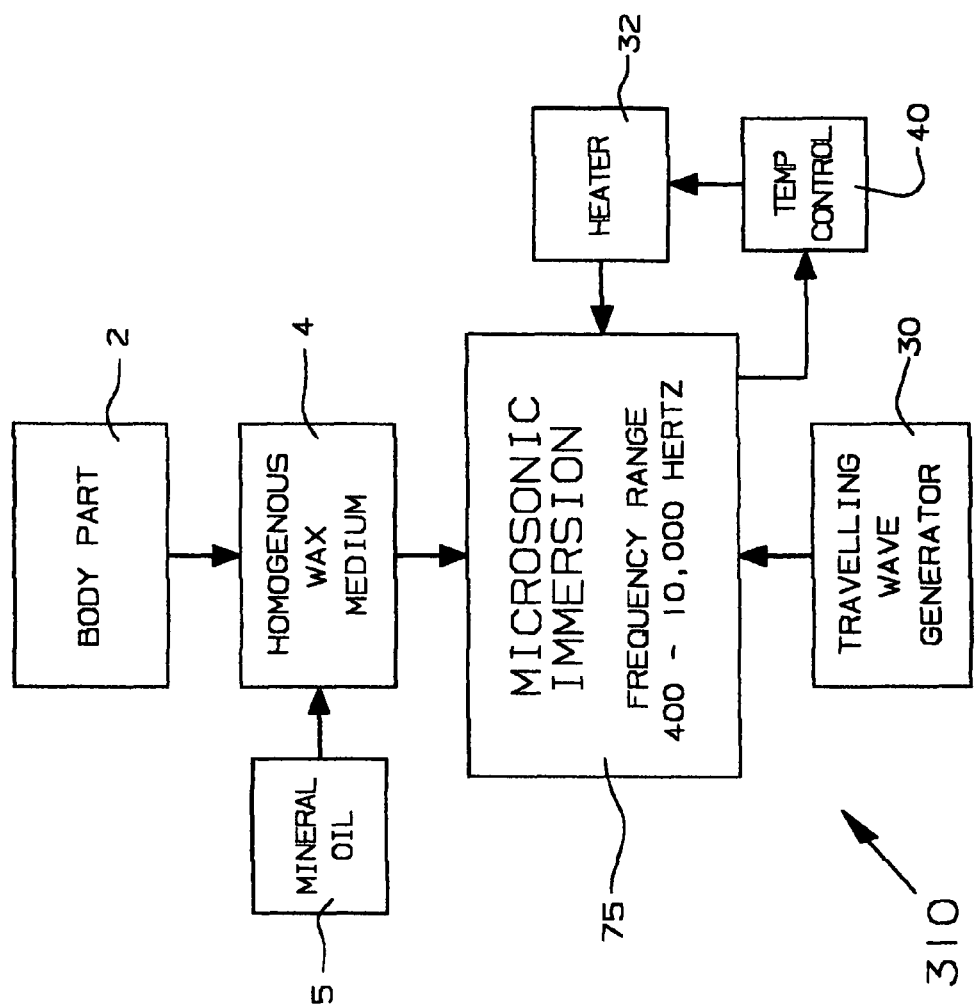
FIG. 14 is a block diagram of the present invention method of applying a heated or unheated vibrating homogenous medium to a body part of a user.

Referring to FIG. 14, there is shown at 310 the present invention method of a microsonic immersion block diagram. The method 310 comprising: a body part 2, a homogenous wax medium 4, mineral oil or additives 5, a microsonic immersion frequency 75, heating means 32, a traveling wave generator 30, and a temperature control 40.

The apparatus conforms to conventional forms of manufacture, or any other conventional way known to one skilled in the art. The manufacturing process which could accommodate the construction of the present invention apparatus may be injection, thermoform, etc. or other molding process.

Figure 16:
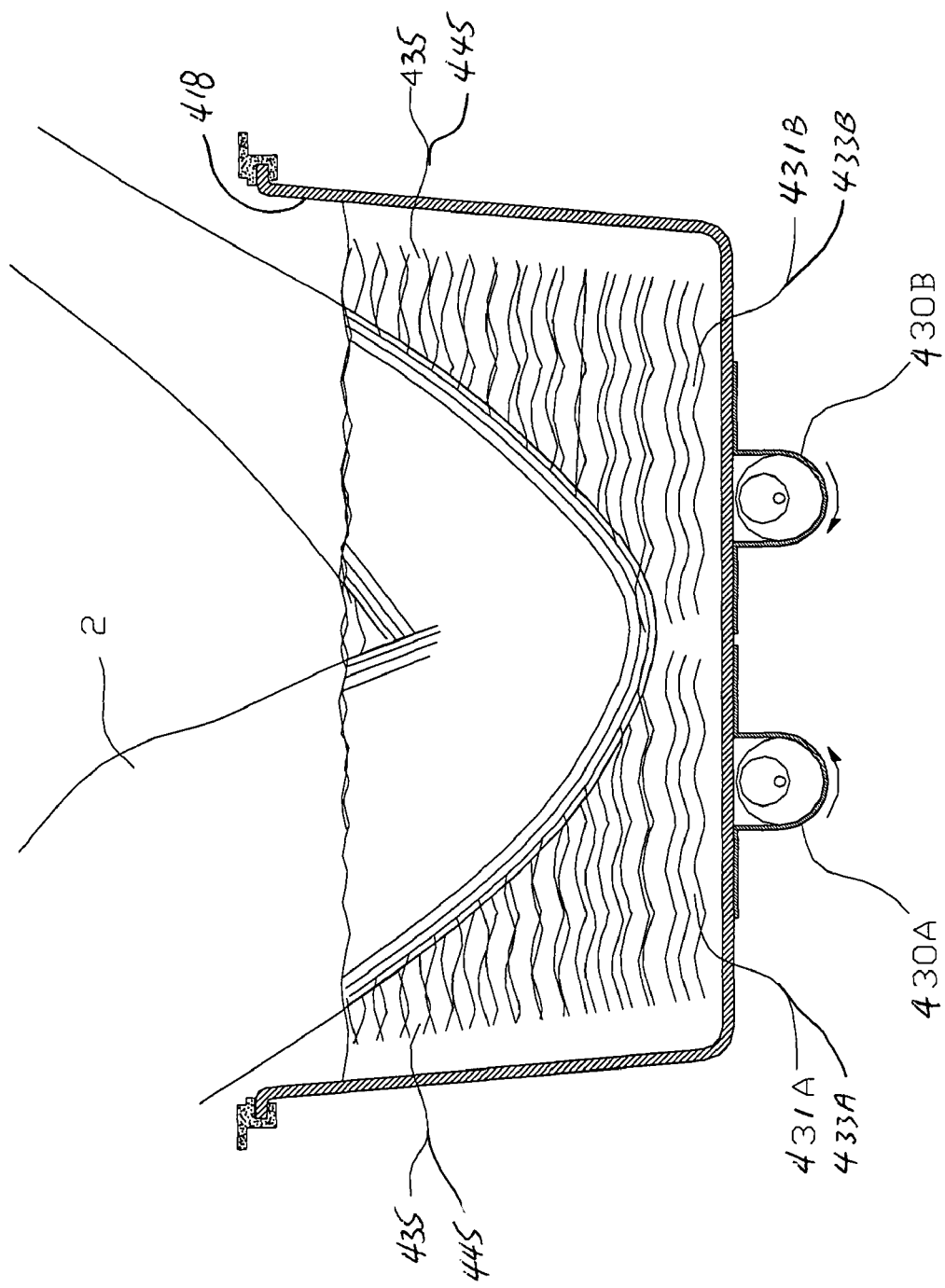
FIG. 16 shows a cross-sectional view of the present invention therapeutic apparatus, showing a body part immersed in a homogenous medium which is combined with two traveling waves combined to create a constructive and destructive pulse wave from the two traveling waves.

Referring to FIG. 16, there is shown the present invention therapeutic apparatus 410 that is very similar to the previous embodiments discussed above and the only difference is the nature and configuration of the vibration generators 430A and 430B. All of the identical parts of this embodiment of the invention therapeutic apparatus 410 are numbered correspondingly with 400 added to each number.

The present invention is a therapeutic apparatus for generating at least two wave forms at two distinct areas of the vibratory vessel 418 of the container, where the waveforms are converging on each other and combine together to create a destructive wave (lower amplitude from the original waveform), a constructive wave (larger amplitude from the original waveform) or both (lower and larger amplitudes from the original waveforms).

Figure 17:
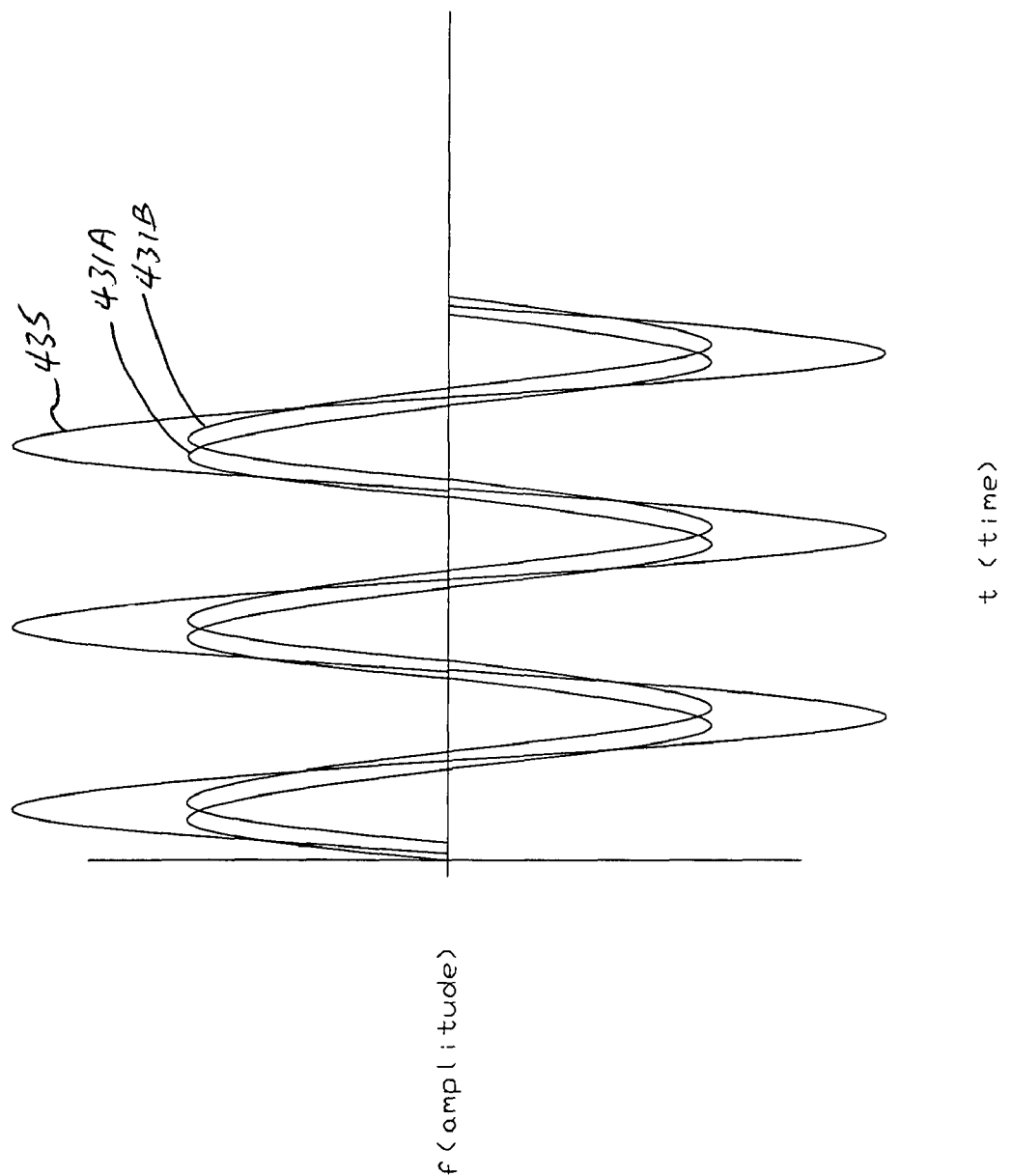
FIG. 17 is an illustrative diagram showing two non-turbulent traveling waves which are combined to form a constructive wave having constructive amplitude which is greater than the amplitude of the two non-turbulent traveling waves.

Referring to FIG. 17, there is illustratively shown two non-turbulent waves 430A and 430B in constructive harmony, where the two waves are combined together and create a constructive waveform 435 having higher amplitude of the harmony from the two original waves 430A and 430B. According to the present invention, when there is a distribution of resonant modes of a first non-turbulent wave 430A over one area and there is another distribution of resonant modes of a second non-turbulent wave 430B over another area, then there will be a distribution of resonant modes of a constructive pulse wave 435 which is produced by the resonance or interaction of the first and second non-turbulent waves 430A and 430B.

Figure 18:
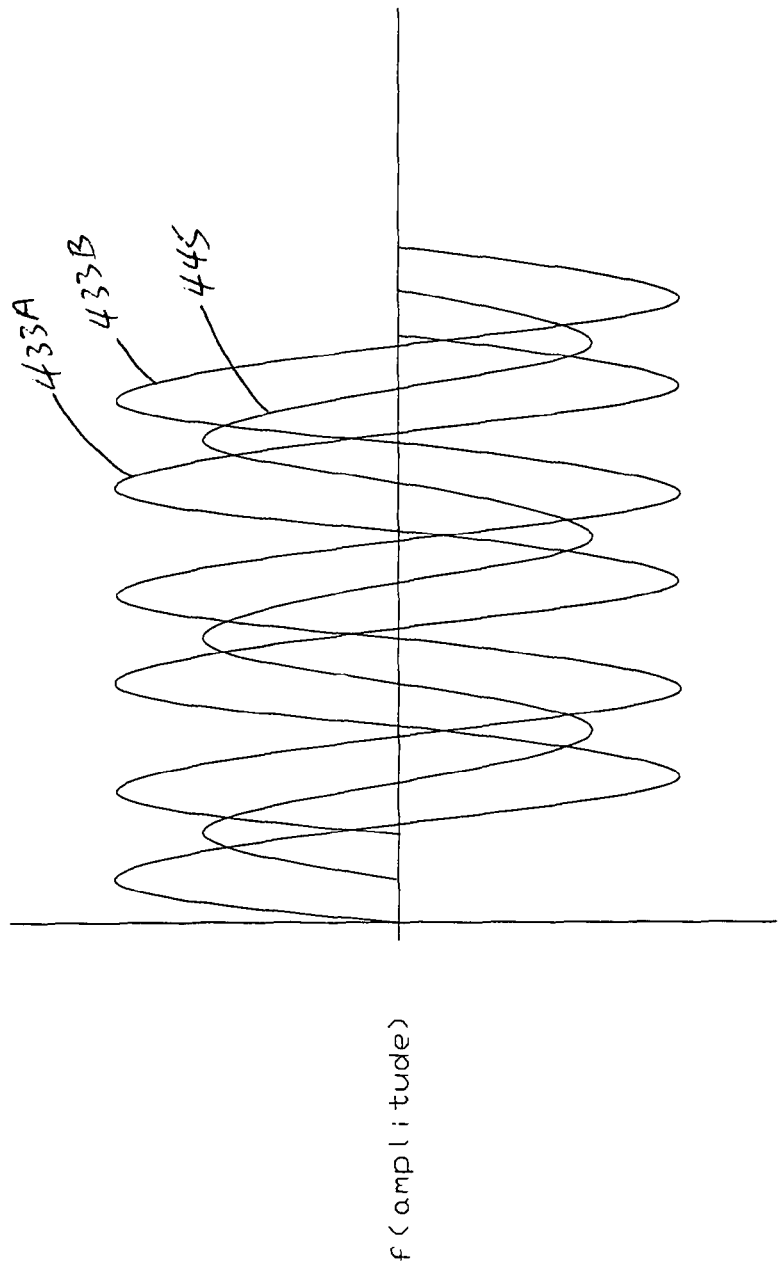
FIG. 18 is an illustrative diagram showing two non-turbulent traveling waves which are combined to form a destructive wave having a destructive amplitude which is less than the amplitude of the two non-turbulent traveling waves.

Referring to FIG. 18, there is illustratively shown two non-turbulent waves 440A and 440B in a destructive harmony, where the two waves are combined together and create a destructive waveform 445 having lower amplitude of the harmony from the two original waves 440A and 440B.

Referring to FIG. 19, there is a graph illustratively showing a constructive (rising) and destructive (falling) pulse wave from the combined two original waves shown in FIGS. 17 and 18.

Figure 15:
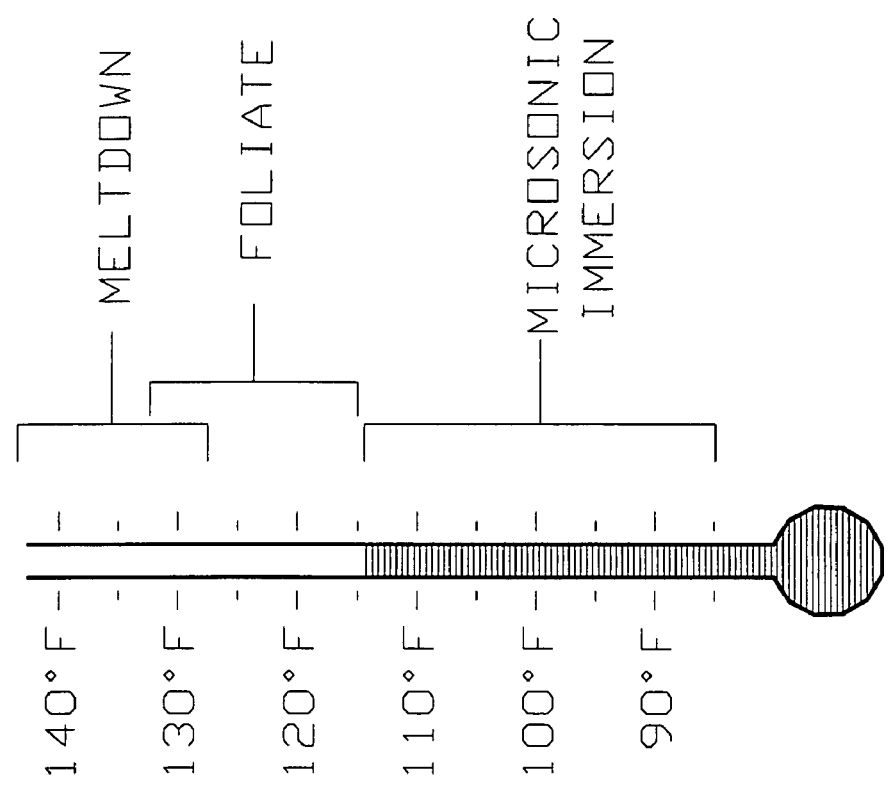
FIG. 15 is a graph showing the temperature range of the microsonic immersion, the foliate temperature range and the meltdown temperature range of the homogenous wax medium in accordance with the present invention.

The heating means are shown in previous embodiment and can heat the homogenous wax medium to a temperature range of 125° F. to 145° F. (see FIG. 15) so that the semi-solid wax can be melted into a hot homogenous wax medium. Once the semi-solid wax has been melted down, the heating means can be set at a temperature range of 85° F. to 115° F. so that the body part 2 of the user can immerse into the heated homogenous wax medium for prolong periods of time without concern of being burn from the heated homogenous wax medium. The heating means are located on the exterior surface of the vibratory vessel. They can be on the sidewall or bottom wall of the vibratory vessel in order to provide more even heat distribution and to provide enhanced safety to that a body part of a user does not rest near or touch the heating means. The control panel may be a computerized control panel for automatically controlling the operation of the therapeutic apparatus.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A synergistic apparatus for providing therapeutic benefits of heat, emollients and cascading vibratory massage both continuously and comfortably to a body part of a user, comprising:
   (a) a container having a bottom wall and a sidewall which extends upwardly from the bottom wall to form an upper lip and opening for retaining and isolating a vibratory vessel having a sidewall which is interior of and spaced apart from the sidewall of the container and a bottom wall which is interior of and spaced apart from the bottom wall of the container so that a space is formed between the respective bottom walls and sidewalls;
   (b) means for isolating said container from said vibratory vessel is an elastomeric isolator disposed between the vibratory vessel and the container for isolating said vibratory vessel's heat and vibration from said container;
   (c) said vibratory vessel containing a combination of a homogenous wax medium and mineral oil which the body part is immersed, the vibratory vessel being of sufficient size so that the body part does not touch the sidewall or the bottom wall of said vibratory vessel when the body part is immersed into the combination of the homogenous wax medium and mineral oil;
   (d) means for heating said vibratory vessel located on an exterior surface of said vibratory vessel within the space between said vibratory vessel and said container to provide even heat distribution and enhanced safety to the user;
   (e) said heating means heating at a mix melting point for said combination of the homogenous wax medium and mineral oil contained within said vibratory vessel to a temperature range approximately 85° F. to 115° F. to allow continuous prolong body part immersion to remain in said combination of the homogenous wax medium and mineral oil for an extended period of time to provide therapeutic treatment;
   (f) at least two vibration generators mounted parallel and opposing each other on said bottom wall of said vibratory vessel and located within the space between said vibratory vessel and said container, the at least two vibration generators vibrating said vibratory vessel to generate first and second non-turbulent traveling waves within said combination of the homogenous wax medium and mineral oil, each traveling wave having a specific frequency and an amplitude, where the first and second non-turbulent traveling waves are converging on each other and combining together to create a harmonic constructive and destructive pulse wave having a larger constructive amplitude than the amplitude of the first and second traveling waves and a smaller destructive amplitude than the amplitude of the first and second traveling waves for providing the harmonic constructive and destructive pulse wave massaging effect to the body part of the user immersed within said combination of the homogenous wax medium and mineral oil contained within said vibratory vessel; and
   (g) a synergistic combination of said vibratory vessel, said at least two vibration generators, said heating means and said temperature range in combination with said homogenous wax medium and mineral oil creating permeability of a body part and deep penetration of heat, vibration and oil therapy to the body part immersed in said combination of the homogenous wax medium and mineral oil;
   (h) whereby the body part is immersed within said combination of the homogenous wax medium and mineral oil contained within said vibratory vessel such that the body part does not touch the walls of said vibratory vessel and when said apparatus is activated, said combination of the homogenous wax medium and mineral oil are heated to a level wherein the body part remains in said combination of the homogenous wax medium and mineral oil for a period of time to provide enhanced therapeutic treatments to the body part immersed in said combination of the homogenous wax medium and mineral oil contained within said vibratory vessel.

2. The apparatus in accordance with claim 1, further comprising means for sensing the temperature of said combination of the homogenous wax medium and mineral oil contained within said vibratory vessel.

3. The apparatus in accordance with claim 2, wherein said temperature sensing means is controlled by a computerized control panel.

4. The apparatus in accordance with claim 1, wherein said means for isolating said container from said vibratory vessel is a ledge on said vibratory vessel at the location of the upper lip of the sidewall of said container.

5. The apparatus in accordance with claim 1, wherein the shape of said vibratory vessel is circular.

6. A synergistic apparatus for providing therapeutic benefits of heat, emollients and cascading vibratory massage both continuously and comfortably to a body part of a user, comprising:
   (a) a container having a bottom wall and a sidewall which extends upwardly from the bottom wall to form an upper lip and opening for retaining and isolating a vibratory vessel having a sidewall which is interior of and spaced apart from the sidewall of the container and a bottom wall which is interior of and spaced apart from the bottom wall of the container so that a space is formed between the respective bottom walls and sidewalls;
   (b) means for isolating said container from said vibratory vessel is an elastomeric isolator disposed between the vibratory vessel and the container for isolating said vibratory vessel's heat and vibration from said container;
   (c) said vibratory vessel containing a homogenous wax medium into which the body part is immersed, the vibratory vessel being sufficient in size so that the body part does not touch the sidewall or the bottom wall of said vibratory vessel when the body part is immersed into the homogenous wax medium;

(d) means for heating said vibratory vessel located on an exterior surface of said vibratory vessel within the space between said vibratory vessel and said container to provide even heat distribution and enhanced safety to the user, the heating means heating at a mix melting point for said homogenous wax medium contained within said vibratory vessel to a temperature range of approximately 85° F. to 115° F. to allow continuous prolong body part immersion to remain in said homogenous wax medium for an extended period of time to provide therapeutic treatment;

(e) at least two vibration motors mounted parallel and opposing each other on said bottom wall of said vibratory vessel for vibrating said vibratory vessel to generate first and second non-turbulent traveling waves within said homogenous wax medium, each traveling wave having a specific frequency and an amplitude, where the first and second non-turbulent traveling waves are converging on each other and combining together to create a harmonic constructive and destructive pulse wave having a larger constructive amplitude than the amplitude of the first and second traveling waves and a smaller destructive amplitude than the amplitude of the first and second traveling waves for providing the harmonic constructive and destructive pulse wave massaging effect to the body part of the user immersed within said homogenous wax medium contained within said vibratory vessel; and (f) a synergistic combination of said vibratory vessel, said at least two vibration motors, and said temperature range in combination with said homogenous wax medium creating permeability of a body part and deep penetration of heat and vibration to the body part immersed in said homogenous wax medium;

(g) whereby the body part is immersed within said homogenous wax medium contained within said vibratory vessel such that the body part does not touch the walls of said vibratory vessel and when said apparatus is activated, said homogenous wax medium is heated to a level wherein the body part remains in said homogenous wax medium for a period of time to provide enhanced therapeutic treatments to the body part immersed in said homogenous wax medium contained within said vibratory vessel.

7. The apparatus in accordance with claim 6, further comprising means for sensing the temperature of said homogenous wax medium contained within said container.

8. The apparatus in accordance with claim 7, wherein said temperature sensing means is controlled by a computerized control panel.

9. The apparatus in accordance with claim 6, wherein said means for isolating the container from the vibratory vessel is a ledge on the vibratory vessel at the location of the upper lip of the sidewall of the container.

10. The apparatus in accordance with claim 6, wherein the shape of said vibratory vessel is circular.

11. A synergistic apparatus for providing therapeutic benefits of heat, emollients and cascading vibratory massage both continuously and comfortably to a body part of a user, comprising:

(a) a container having a bottom wall and a sidewall which extends upwardly from the bottom wall to form an upper lip and opening for retaining and isolating a vibratory vessel having a sidewall which is interior of and spaced apart from the sidewall of the container and a bottom wall which is interior of and spaced apart from the bottom wall of the container so that a space is formed between the respective bottom walls and sidewalls;

(b) means for isolating said container from said vibratory vessel is an elastomeric isolator disposed between the vibratory vessel and the container for isolating said vibratory vessel's heat and vibration from said container;

(c) said vibratory vessel containing a semi-solid wax medium and into which the body part is immersed, said vibratory vessel being of sufficient size so that the body part does not touch the sidewall or the bottom wall of the vibratory vessel when the body part is immersed into the semi-solid wax medium;

(d) means for heating said vibratory vessel located on an exterior surface of said vibratory vessel within the space between said vibratory vessel and said container to provide even heat distribution and enhanced safety to the user, the heating means heating at a mix melting point for said semi-solid wax medium contained within said vibratory vessel to a temperature range approximately 85° F. to 115° F. to allow continuous prolong body part immersion to remain in said semi solid wax medium for an extended period of time to provide therapeutic treatment; and (e) at least two motors mounted parallel and opposing each other on said bottom wall of said vibratory vessel for vibrating said vibratory vessel to generate first and second non-turbulent traveling waves within said semi-solid wax medium, each traveling wave having a specific frequency and an amplitude, where the first and second non-turbulent traveling waves are converging on each other and combining together to create a harmonic constructive and destructive pulse wave having a larger constructive amplitude than the amplitude of the first and second traveling waves and a smaller destructive amplitude than the amplitude of the first and second traveling waves for providing the harmonic constructive and destructive pulse wave massaging effect to the body part of the user immersed within said semi-solid wax medium contained within said vibratory vessel;

(f) a synergistic combination of said vibratory vessel, said at least two motors, said heating means and said temperature range in combination with said semi-solid wax medium creating permeability of a body part and deep penetration of heat, vibration and oil therapy to the body part immersed in said semi-solid wax medium;

(g) whereby the body part is immersed within said semi-solid wax medium contained within said vibratory vessel such that the body part does not touch the walls of said vibratory vessel and when said apparatus is activated, said semi-solid wax medium is heated to a level wherein the body part remains in said semi-solid wax medium for a period of time to provide enhanced therapeutic treatments to the body part immersed in said semi-solid wax medium contained within said vibratory vessel.

12. The apparatus in accordance with claim 11, further comprising means for sensing the temperature of said semi-solid wax medium contained within said container.

13. The apparatus in accordance with claim 12, wherein said temperature sensing means is controlled by a computerized control panel.

14. The apparatus in accordance with claim 11, wherein said means for isolating said container from said vibratory vessel is a ledge on said vibratory vessel at the location of the upper lip of the sidewall of said container.

15. The apparatus in accordance with claim 11, wherein the shape of said vibratory vessel is circular.

* * * * *